(12) United States Patent
Fricker et al.

(10) Patent No.: US 6,565,859 B1
(45) Date of Patent: May 20, 2003

(54) GALENICAL FORMULATIONS

(75) Inventors: Gerd Fricker, Staufen (DE); Barbara Haeberlin, Riehen (CH); Armin Meinzer, Freiburg/Munzingen (DE); Jacky Vonderscher, Fiedisheim (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/532,999

(22) Filed: Mar. 22, 2000

Related U.S. Application Data

(63) Continuation of application No. 09/324,489, filed on Jun. 2, 1999, now abandoned, which is a continuation of application No. 08/916,243, filed on Aug. 22, 1997, now Pat. No. 5,932,243, which is a continuation of application No. 08/248,993, filed on May 25, 1994, now abandoned.

(30) Foreign Application Priority Data

May 27, 1993 (GB) ............................................... 9310974
Oct. 5, 1993 (GB) ............................................... 9320463

(51) Int. Cl.⁷ ................................................ A61K 9/107
(52) U.S. Cl. .................... 424/400; 514/11; 514/937; 514/938; 514/941
(58) Field of Search .................... 424/450, 400; 514/11, 937, 938–943

(56) References Cited

U.S. PATENT DOCUMENTS

| | | | |
|---|---|---|---|
| 3,929,992 A | 12/1975 | Sehgal et al. | |
| 4,388,307 A | 6/1983 | Cavanak | |
| 4,719,239 A | 1/1988 | Muller et al. | |
| 4,831,018 A | 5/1989 | Kirsh et al. | |
| 4,987,139 A | 1/1991 | Chen et al. | |
| 5,104,871 A | 4/1992 | Bell et al. | |
| 5,169,851 A | 12/1992 | Hughes et al. | |
| 5,190,950 A | 3/1993 | Beattie et al. | |
| 5,206,018 A | 4/1993 | Sehgal et al. | |
| 5,215,995 A | 6/1993 | Honbo et al. | |
| 5,318,895 A | 6/1994 | Kahn et al. | |
| 5,342,625 A | 8/1994 | Hauer et al. | |
| 5,510,118 A | 4/1996 | Bosch et al. ............... | 424/489 |
| 5,534,270 A | 7/1996 | De Castro .................. | 424/490 |
| 5,536,729 A | 7/1996 | Waranis et al. ........... | 514/291 |
| 5,559,121 A | 9/1996 | Harrison et al. .......... | 514/291 |
| 5,741,512 A * | 4/1998 | Hauer ....................... | 424/450 |
| 5,932,243 A * | 8/1999 | Fricker ..................... | 426/450 |

FOREIGN PATENT DOCUMENTS

| | | |
|---|---|---|
| BE | 895724 | 7/1983 |
| CA | 2133177 | 3/1995 |
| CH | 679118 | 12/1991 |
| DE | 43 22 826 | 1/1995 |
| DE | 43 29 503 | 3/1995 |
| EP | 41795 | 12/1981 |
| EP | 041 795 | 12/1981 |
| EP | 184162 | 6/1986 |
| EP | 302370 | 2/1989 |
| EP | 202837 | 10/1989 |
| EP | 361928 | 4/1990 |
| EP | 401747 | 12/1990 |
| EP | 423 714 | 4/1991 |
| EP | 427680 | 5/1991 |
| EP | 428169 | 5/1991 |
| EP | 444659 | 9/1991 |
| EP | 483842 | 5/1992 |
| EP | 499 299 | 8/1992 |
| EP | 532862 | 3/1993 |
| EP | 533433 | 3/1993 |
| EP | 552031 | 7/1993 |
| EP | 577 215 | 1/1994 |
| EP | 648 494 | 4/1995 |
| EP | 649 659 | 4/1995 |
| EP | 650 730 | 5/1995 |
| EP | 868 911 | 10/1998 |
| EP | 589843 | 11/2001 |
| GB | 907430 | 10/1962 |
| GB | 1322306 | 7/1973 |
| GB | 2015339 | 9/1979 |
| GB | 2221157 | 1/1990 |
| GB | 2222770 | 3/1990 |
| GB | 2247620 | 3/1992 |
| GB | 2248184 | 4/1992 |
| GB | 2249027 | 4/1992 |
| GB | 2257359 | 1/1993 |
| GB | 2271121 | 4/1994 |
| JP | 9048737 | 2/1997 |
| PT | 95230 | 3/1983 |
| WO | 90/14094 | 11/1990 |
| WO | 91/19495 | 12/1991 |
| WO | 92/14737 | 9/1992 |
| WO | WO 92/18105 | 10/1992 |
| WO | 92/18105 | 10/1992 |
| WO | 92/21341 | 12/1992 |
| WO | 93/20833 | 10/1993 |
| WO | WO 96/13273 | 5/1996 |
| WO | WO 96/25150 | 8/1996 |
| WO | WO 97/03654 | 2/1997 |
| WO | WO 98/56358 | 12/1998 |

OTHER PUBLICATIONS

Charman et al, Pharm. Res., vol. 9, No. 1, 87–92 (1992).*
Charman et al., Pharm. Res., vol. 9, No. 1, 87–92 (1992).
Chemical Abstract JP 85–133882 Jun. 19, 1985.

* cited by examiner

*Primary Examiner*—Gollamudi S. Kishore
(74) *Attorney, Agent, or Firm*—Gabriel Lopez

(57) ABSTRACT

A pharmaceutical composition containing macrolide, e.g. a rapamycin compound in an emulsion preconcentrate or microemulsion preconcentrate for oral administration. The carrier medium for the rapamycin compound includes a hydrophilic phase, a lipophilic phase and a surfactant. The composition is stable and provides high absorption efficiency.

7 Claims, No Drawings

GALENICAL FORMULATIONS

This application is a continuation of Ser. No. 09/324,489 filed Jun. 2, 1999, now abandoned, which is a continuation of Ser. No. 08/916,243 filed Aug. 22, 1997, now U.S. Pat. No. 5,932,263 which is a continuation of Ser. No. 08/248,993 filed May 25, 1996, now abandoned.

This invention relates to galenic formulations containing macrolides, e.g. compounds of the rapamycin class. In particular this invention relates to galenic formulations which are in the form of micro-emulsions, micro-emulsion preconcentrates, emulsion or emulsion-preconcentrate.

The macrolide may contain e.g. 1, 2 or 3 ring oxygen or nitrogen or other atoms besides carbon atoms. It may have side chains, e.g. in the form of fused rings, or substituents, e.g. oxy groups. It may contain double bonds. It may contain e.g. from 15 to 35 ring atoms e.g. of carbon.

Rapamycin is a macrolide antibiotic produced by *Streptomyces hygroscopicus*. It has been found to be pharmaceutically useful in a variety of applications, particularly as an immunosuppressant for use in the treatment and prevention of organ transplant rejection and autoimmune diseases. Rapamycin has the following structure:

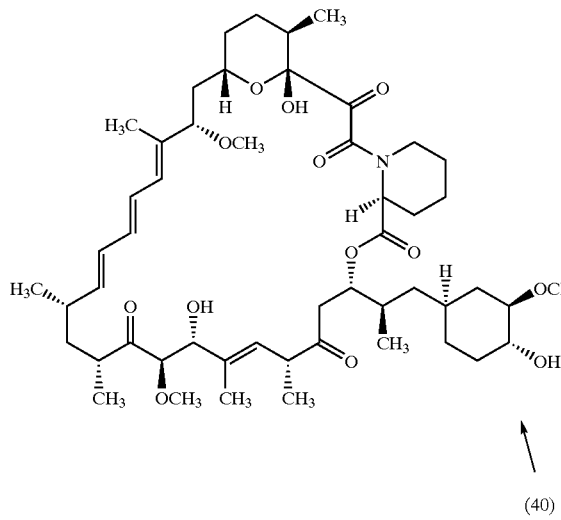

(40)

(Kesseler, H., et al., Helv. Chim. Acta (1993) 76: 117; U.S. Pat. No. 3,929,992). Large numbers of derivatives of rapamycin have been synthesized, including for example those disclosed in U.S. Pat. Nos. 5,221,670 and 5,221,740, certain acyl and aminoacyl-rapamycins (see for example U.S. Pat. No. 4,316,885, U.S. Pat. No. 4,650,803, and U.S. Pat. No. 5,151,413), and carbonates and amide esters (see for example EP 509795 and 515140) 27-desmethyl-rapamycin (see for example WO 92/14737), 26-dihydro-rapamycin (see for example U.S. Pat. No. 5,138,051), alkoxyester derivatives (see for example U.S. Pat. No. 5,233,036), and certain pyrazole derivatives (U.S. Pat. No. 5,164,399).

Rapamycin and its structurally similar analogs and derivatives are termed collectively as "compounds of the rapamycin class" in this specification.

Compounds of the rapamycin class are extremely potent immunosuppressants and have also been shown to have antitumor and antifungal activity. However their utility as pharmaceuticals especially on oral administration has been restricted by their very low solubility, low and variable bioavailability and their high toxicity. Little is known concerning the causes of these properties and the site of absorption. Thus low bioavailability may be thought to due to due to extensive metabolism of the macrolide ring and not solvable by a galenical formulation. Therefore there is a need for an acceptable pharmaceutical composition that contains compounds of the rapamycin class.

FK506 is a macrolide immunosuppressant that is produced by *Streptomyces tsukubaensis* No 9993. The structure of FK506 is given in the appendix to the Merck Index, as item A5. Also a large number of related compounds which retrain the basic structure and immunological properties of FK506 are also known. These compounds are described in a large number of publications, for example EP 184162, EP 315973, EP 323042, EP 423714, EP 427680, EP 465426, EP 474126, WO 91/13889, WO 91/19495, EP 484936, EP 532088, EP 532089, WO 93/5059 and the like. Little is known concerning the biopharmaceutical properties of such compounds. These compounds are termed collectively "FK506 compounds" in this specification.

It has now been surprisingly found that stable compositions containing macrolides that offer high absorption efficiency, can be obtained by formulating the macrolide with certain carrier media.

Accordingly, this invention provides a pharmaceutical composition comprising a macrolide and a carrier medium comprising a hydrophilic phase, a lipophilic phase and a surfactant.

In another aspect the invention provides a pharmaceutical composition which comprises an orally administrable active agent which is other than a cyclosporin and a microemulsion preconcentrate carrier medium therefor which comprises i) a reaction product of castor oil and ethylene oxide,
ii) a transesterification product of a vegetable oil and glycerol comprising predominantly linoleic acid or oleic acid mono-, di- and tri-glycerides, or a polyoxyalkylated vegetable oil,
iii) 1,2 propylene glycol and
iv) ethanol.

The pharmaceutical composition is stable and results in surprisingly high and consistent absorption efficiency when administered orally. Therefore the macrolide may be administered in lower doses, which alleviates toxicity problems. For example, in animal trials in which the pharmaceutical compositions are administered orally, the pharmaceutical compositions resulted in high bioavailabilities. Hence the pharmaceutical compositions have very surprising properties which offer great advantages.

Preferably the composition is in the form of a "microemulsion preconcentrate" or "emulsion preconcentrate", in particular of the type providing o/w (oil-in-water) microemulsions or emulsions. However the composition may be in the form of a microemulsion or an emulsion which additionally contains an aqueous phase; preferably water.

A "microemulsion preconcentrate" is defined in this specification as being a formulation which spontaneously forms a microemulsion in an aqueous medium, for example, in water or in the gastric juices after oral application.

A "microemulsion" is a non-opaque or substantially non-opaque colloidal dispersion that is formed spontaneously or substantially spontaneously when its components are brought into contact. A microemulsion is thermodynamically stable and contains dispersed particles of a size less than about 2000 Å. Generally microemulsions comprise droplets or particles having a diameter of less than about 1500 Å; typically from 30 to 1000 Å. Further characteristic can be found in British patent application 2 222 770 A; the disclosure of which is incorporated herein by reference.

An "emulsion preconcentrate" is defined in this specification as being as being a formulation which spontaneously forms an emulsion in an aqueous medium, for example, in water or in the gastric juices after oral application. The emulsion formed is opaque, thermodynamically stable and contains dispersed droplets of a size greater than about 100 nm, more usually greater than about 200 nm. Often bimodal size range distributions are obtained. The emulsion preconcentrates are preferably of the type providing o/w (oil-in-water) emulsions.

A "pharmaceutical composition" means a composition in which the individual components or ingredients are themselves pharmaceutically acceptable and, when a particular form of administration is foreseen, are suitable or acceptable for that form of administration.

The lipophilic phase may comprise 10 to 85% by weight of the carrier medium; preferably 15 to 70% by weight, more preferably 20 to 60% by weight and even more preferably about 25% by weight.

The surfactant may comprise 5 to 80% by weight of the carrier medium; preferably 10 to 70% by weight, more preferably 20 to 60% by weight and even more preferably about 40% by weight.

The hydrophilic phase may comprise 10 to 50% by weight of the carrier medium; preferably 15 to 40% by weight, more preferably 20 to 35% by weight and even more preferably about 30% by weight.

The macrolide is preferably present in an amount of 1 to 15% by weight of the composition; more preferably about 2 to 10%.

The macrolide may be rapamycin or an O-substituted derivative in which the hydroxy in position 40 of the formula illustrated above is replaced by —$OR_1$ in which $R_1$ is hydroxyalkyl, hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)-rapamycin. These O-substituted derivatives may be produced by reacting Rapamycin (or dihydro or deoxorapamycin) with an organic radical attached to a leaving group (for example RX where R is the organic radical which is desired as the O-substituent, such as an alkyl, allyl, or benzyl moiety, and X is a leaving group such as $CCl_3C(NH)O$ or $CF_3SO_3$) under suitable reaction conditions. The conditions may be acidic or neutral conditions, for example in the presence of an acid like trifluoromethane-sulfonic acid, camphorsulfonic acid, p-toluenesulfonic acid or their respective pyridinium or substituted pyridinium salts when X is $CCl_3C(NH)O$ or in the presence of a base like pyridine, a substituted pyridine, diisopropylethylamine or pentamethylpiperidine when X is $CF_3SO_3$.

A preferred compound is 40-O-(2-hydroxy)ethyl rapamycin (hereinafter compound A) as disclosed in PCT/EP/93/02604.

Examples of compounds of the FK 506 class are those mentioned above. They include for example FK 506, ascomycin and other naturally occuring compounds. They include also synthetic analogues.

A preferred compound of the FK 506 class is disclosed in EP 427 680, e.g. Example 66a. Other preferred compounds are disclosed in EP 465 426.

The hydrophilic phase may be selected from Transcutol (which has the formula $C_2H_5$—[O—$(CH_2)_2$]$_2$—OH), Glycofurol (also known as tetrahydrofurfuryl alcohol polyethylene glycol ether) and 1,2-propylene glycol, or mixtures thereof, and is preferably 1,2-propylene glycol. The hydrophilic phase may include further hydrophilic co-components, for example lower alkanols such as ethanol. These co-components will generally be present in partial replacement of other components of the hydrophilic phase. While the use of ethanol in the compositions is not essential, it has been found to be of particular advantage when the compositions are to be manufactured in soft gelatine, encapsulated form. This is because storage characteristics are improved, in particular the risk of rapamycin precipitation following encapsulation procedures is reduced. Thus the shelf life stability may be extended by employing ethanol or some other such co-component as an additional ingredient of the hydrophilic phase. The ethanol may comprise 0 to 60% by weight of the hydrophilic phase; preferably 20 to 55% by weight and more preferably about 40 to 50% by weight. Small quantities of liquid polyethylene glycols may also be included in the hydrophilic phase.

Preferred lipophilic phase components are medium chain fatty acid triglycerides, mixed mono-, di-, tri-glycerides, and transesterified ethoxylated vegetable oils.

Suitable medium chain fatty acid triglycerides are those known and commercially available under the trade names Miglyol, Captex, Myritol, Capmul, Captex, Neobee and Mazol; Miglyol 812 being the most preferred. These triglycerides are described in Fiedler, H. P. "Lexikon der Hilfsstoffe für Pharmazie, Kosmetik und angrenzende Gebiete", Editio Cantor, D-7960 Aulendorf, 3rd revised and expanded edition (1989), the contents of which are hereby incorporated by reference.

The mixed mono-, di-, tri-glycerides preferably comprise mixtures of $C_{12-20}$ fatty acid mono-, di- and tri-glycerides, especially mixed $C_{16-18}$ fatty acid mono-, di- and triglycerides. The fatty acid component of the mixed mono-, di- and tri-glycerides may comprise both saturated and unsaturated fatty acid residues. Preferably however they are predominantly comprised of unsaturated fatty acid residues; in particular $C_{18}$ unsaturated fatty acid residues. Suitably the mixed mono-, di-, tri-glycerides comprise at least 60%, preferably at least 75%, more preferably at least 85% by weight of a $C_{18}$ unsaturated fatty acid (for example linolenic, linoleic and oleic acid) mono-, di- and tri-glycerides. Suitably the mixed mono-, di-, tri-glycerides comprise less than 20%, for example about 15% or 10% by weight or less, saturated fatty acid (for example palmitic and stearic acid) mono-, di- and tri-glycerides.

The mixed mono-, di-, tri-glycerides are preferably predominantly comprised of mono- and di-glycerides; for example mono- and di-glycerides comprise at least 50%, more preferably at least 70% based on the total weight of the lipophilic phase. More preferably, the mono- and di-glycerides comprise at least 75% (for example about 80% or 85% by weight of the lipophilic phase.

Preferably the monoglycerides comprise from about 25 to about 50%, based on the total weight of the lipophilic phase, of the mixed mono-, di-, tri-glycerides. More preferably from about 30 to about 40% (for example 35 to 40%) monoglycerides are present.

Preferably the diglycerides comprise from about 30 to about 60%, based on the total weight of the lipophilic phase, of the mixed mono-, di-, tri-glycerides. More preferably from about 40 to about 55% (for example 48 to 50%) diglycerides are present.

The triglycerides suitably comprise at least 5% but less than about 25%, based on the total weight of the lipophilic phase, of the mixed mono-, di-, tri-glycerides. More preferably from about 7.5 to about 15% (for example from about 9 to 12%) triglycerides are present.

The mixed mono-, di-, tri-glycerides may be prepared by admixture of individual mono-, di- or tri-glycerides in appropriate relative proportion. Conveniently however they comprise transesterification products of vegetable oils, for example almond oil, ground nut oil, olive oil, peach oil, palm oil or, preferably, corn oil, sunflower oil or safflower oil and most preferably corn oil, with glycerol.

Such transesterification products are generally obtained by heating the selected vegetable oil with glycerol, at high temperature in the presence of an appropriate catalyst under an inert atmosphere with continuous agitation (for example in a stainless steel reactor) to effect trans-esterification or glycerolysis. In addition to their mono-, di- and tri-glyceride components, the transesterification products also generally comprise minor amounts of free glycerol. The amount of free glycerol present is preferably less than 10%, more preferably less than 5%, most preferably about 1 or 2% by weight based on the total weight of free glycerol plus mono-, di- and tri-glycerides.

Preferably some of the glycerol is first removed to give a "substantially glycerol free batch" when soft gelatine capsules are to be made.

Trans-esterification products of corn oil and glycerol provide particularly suitable mixed mono-, di-, and tri-glycerides. An example of a suitable mixed glyceride product is the trans-esterification product commercially available under the trade name MAISINE. This product is comprised predominantly of linoleic and oleic acid mono-, di- and tri-glycerides together with minor amounts of palmitic and stearic acid mono-, di- and tri-glycerides (corn oil itself being comprised of about 56% by weight linoleic acid, 30% oleic acid, about 10% palmitic and about 3% stearic acid constituents). The physical characteristics of MAISINE [available from the company Etablissements Gattefossé, of 36, Chemin de Genas, P.O.Box 603, 69804 Saint-Priest, Cedex (France)] are: up to 10% (typically 3.9 to 4.9% or, in "substantially glycerol free" batches, about 0.2%) free glycerol; about 35% (typically 30 to 40% or, in "substantially glycerol free" batches, about 32 to 36%, for example about 36%) mono-glycerides; about 50% (or, in "substantially glycerol free" batches about 46 to 48%) di-glycerides; about 10% (or, in "substantially glycerol free" batches, about 12 to 15%) tri-glycerides; and about 1% free oleic acid.

Further physical characteristics for MAISINE are: an acid value of maximum about 2, an iodine no. of about 85 to 105, a saponification no. of about 150 to 175 (Fiedler "Lexikon der Hilfsstoffe", 3rd revised and expanded edition (1989) Vol. 2, p.768). The fatty acid content for MAISINE is typically: about 11% palmitic acid; about 2.5% stearic acid; about 29% oleic acid; about 56% linoleic acid; and 1.5% other acids.

It is especially preferred that the mixed mono-, di-, and tri-glycerides are clear and remain clear for more than 20 days upon storage at temperatures of 20° C. to 25° C. Also, a sample of the mixed mono-, di-, and tri-glycerides, which has been kept in a refrigerator at about between 2 and 8° C. for 24 hours and then held at room temperature for 1 hour, should be clear.

Preferably the mono-, di-, tri-glycerides have a low saturated fatty acid content. Mixed mono-, di-, tri-glycerides meeting these requirements may be obtained from commercially available products by separation techniques as known in the art (for example freezing procedures coupled with separation techniques such as centrifugation) to remove the saturated fatty acid components and enhance the unsaturated fatty acid component content. Typically the total saturated fatty acid component content will be less than 15%, (for example <10%, or <5%) by weight based on the total weight of the lipophilic phase. A reduction of the content of saturated fatty acid component in the mono-glyceride fraction may be observed after being subjected to the separation technique. A suitable process is described in WO 93/09211.

The mixed mono-, di-, tri-glycerides thus preferably contain lesser quantities of saturated fatty acids (e.g. palmitic and stearic acids) and relatively greater quantities of unsaturated fatty acids (e.g. oleic and linoleic acids) than the starting material.

A suitable example of a mixed mono-, di-, tri-glyceride product containing lesser quantities of saturated fatty acids contains: 32 to 36% mono-glycerides, 45 to 55% di-glycerides and 12 to 20% tri-glycerides, by weight based on the total weight of the lipophilic phase. Further characteristics include the following:

| | |
|---|---|
| Fatty acid content (as determined as the methyl ester by chromatography) | Methyl linoleate 53 to 63%, Methyl oleate 24 to 34%, Methyl linolenate 0 to 3% Methyl arachate 0 to 3%, Methyl palmitate 6 to 12%, Methyl stearate 1 to 3% |
| Relative Density | 0.94 to 0.96 |
| Hydroxyl Value | 140 to 210 |
| Iodine Value | 110 to 20 |
| Peroxide Value | <4.0 |
| Free Glycerol | <1.0 |
| Saponification no | about 150 to 185 |
| Acid value | max. about 2 |

Mixed mono-, di-, tri-glycerides complying with these characteristics are referred to in this specification as "refined glycerol-transesterified corn oils". The "refined glycerol-transesterified corn oils" have the advantage of remaining stable for a long time.

The lipophilic phase may alternatively comprise suitable transesterified ethoxylated vegetable oils such as those obtained by reacting various natural vegetable oils (for example, maize oil, kernel oil, almond oil, ground nut oil, olive oil, soybean oil, sunflower oil, safflower oil and palm oil, or mixtures thereof) with polyethylene glycols that have an average molecular weight of from 200 to 800, in the presence of an appropriate catalyst. These procedures are known and an example is described in U.S. Pat. No. 3,288,824. Transesterified ethoxylated corn oil is particularly preferred.

Transesterified ethoxylated vegetable oils are known and are commercially available under the trade name LABRAFIL (H. Fiedler, loc cit, vol 2, page 707). Examples are LABRAFIL M 2125 CS (obtained from corn oil and having an acid number of less than about 2, a saponification number of 155 to 175, an HLB value of 3 to 4, and an iodine number of 90 to 110), and LABRAFIL M 1944 CS (obtained from kernel oil and having an acid number of about 2, a saponification number of 145 to 175 and an iodine number of 60 to 90). LABRAFIL M 2130 CS (which is a transesterification product of a $C_{12-18}$ glyceride and polyethylene glycol and which has a melting point of about 35 to 40° C., an acid number of less than about 2, a saponification number of 185 to 200 and an iodine number of less than about 3) may also be used. The preferred transesterified ethoxylated vegetable oil is LABRAFIL M 2125 CS which can be obtained, for example, from Gattefossé, Saint-Priest Cedex, France.

Examples of suitable surfactants are:

i) reaction products of a natural or hydrogenated castor oil and ethylene oxide. The natural or hydrogenated castor oil may be reacted with ethylene oxide in a molar ratio of from about 1:35 to about 1:60, with optional removal of the polyethyleneglycol component from the products. Various such surfactants are commercially available. The polyethyleneglycol-hydrogenated castor oils available under the trade name CREMOPHOR are especially suitable. Particularly suitable are CREMOPHOR RH 40, which has a saponification number of about 50 to 60, an acid number less than about 1, a water content (Fischer) less than about 2%, an $n_D^{60}$ of about 1.453 to 1.457 and an HLB of about 14 to 16; and CREMOPHOR RH 60, which has a saponification number of about 40 to 50, an acid number less than about 1, an iodine number of less than about 1, a water content (Fischer) of about 4.5 to 5.5%, an $n_D^{25}$ of about 1.453 to 1.457 and an HLB of about 15 to 17. An especially preferred product of this class is CREMOPHOR RH40. Also suitable are polyethyleneglycol castor oils such as that available under the trade name CREMOPHOR EL, which has a molecular weight (by steam osmometry) of about 1630, a saponification number of about 65 to 70, an acid number of about 2, an iodine number of about 28 to 32 and an $n_D^{25}$ of about 1.471. Similar or identical products which may also be used are available under the trade names NIKKOL (e.g. NIKKOL HCO-40 and HCO-60), MAPEG (e.g. MAPEG CO-40h), INCROCAS (e.g. INCROCAS 40), and TAGAT (e.g. TAGAT RH 40). These surfactants are further described in Fiedler loc. cit.

ii) Polyoxyethylene-sorbitan-fatty acid esters, for example mono- and tri-lauryl, palmityl, stearyl and oleyl esters of the type known and commercially available under the trade name TWEEN (Fiedler, loc. cit. p.1300–1304) including the products TWEEN
20 [polyoxyethylene(20)sorbitanmonolaurate],
21 [polyoxyethylene(4)sorbitanmonolaurate],
40 [polyoxyethylene(20)sorbitanmonopalmitate],
60 [polyoxyethylene(20)sorbitanmonostearate],
65 [polyoxyethylene(20)sorbitantristearate],
80 [polyoxyethylene(20)sorbitanmonooleate],
81 [polyoxyethylene(5)sorbitanmonooleate],
85 [polyoxyethylene(20)sorbitantrioleate].
Especially preferred products of this class are TWEEN 40 and TWEEN 80.

iii) Polyoxyethylene fatty acid esters, for example polyoxyethylene stearic acid esters of the type known and commercially available under the trade name MYRJ (Fiedler, loc. cit., 2, p.834–835). An especially preferred product of this class is MYRJ 52 having a $D^{25}$ of about 1.1., a melting point of about 40 to 44° C., an HLB value of about 16.9., an acid value of about 0 to 1 and a saponification no. of about 25 to 35.

iv) Polyoxyethylene-polyoxypropylene co-polymers and block co-polymers, for example of the type known and commercially available under the trade names PLURONIC, EMKALYX and POLOXAMER (Fiedler, loc. cit., 2, p. 959). An especially preferred product of this class is PLURONIC F68, having a melting point of about 52° C. and a molecular weight of about 6800 to 8975. A further preferred product of this class is POLOXAMER 188.

v) Dioctylsulfosuccinate or di-[2-ethylhexyl]-succinate (Fiedler, loc. cit., 1, p. 107–108).

vi) Phospholipids, in particular lecithins (Fiedler, loc. cit., 2, p. 943–944). Suitable lecithins include, in particular, soya bean lecithins.

vii) Propylene glycol mono- and di-fatty acid esters such as propylene glycol dicaprylate (also known and commercially available under the trade name MIGLYOL 840), propylene glycol dilaurate, propylene glycol hydroxystearate, propylene glycol isostearate, propylene glycol laurate, propylene glycol ricinoleate, propylene glycol stearate and so forth (Fiedler, loc. cit., 2, p. 808–809).

It will also be appreciated that the components of the carrier medium may contain unreacted starting materials, e.g. polyethylene glycol.

The surfactant selected preferably has an HLB of at least 10.

Preferably the relative proportion of hydrophilic phase component(s), the lipophilic phase and the surfactant lie within the "microemulsion" region on a standard three way plot. The compositions thus obtained are microemulsion preconcentrates of high stability that are capable, on addition to water, of providing microemulsions having an average particle size of <1.500 Å and stable over periods in excess of 24 hours.

The microemulsion preconcentrate compositions show good stability characteristics as indicated by standard stability trials, for example having a shelf life stability of up to three years, and even longer.

Alternatively the components may be selected to provide an emulsion preconcentrate. The emulsion preconcentrate compositions also show good stability characteristics as indicated by standard stability trials, for example having a shelf life stability of up to three years, and even longer.

The pharmaceutical composition may also include further additives or ingredients, for example antioxidants (such as ascorbyl palmitate, butyl hydroxy anisole (BHA), butyl hydroxy toluene (BHT) and tocopherols) and/or preserving agents. These additives or ingredients may comprise about 0.05 to 1% by weight of the total weight of the composition. The pharmaceutical composition may also include sweetening or flavoring agents in an amount of up to about 2.5 or 5% by weight based on the total weight of the composition. Preferably the antioxidant is α-tocopherol (vitamin E).

The pharmaceutical composition may also include one or more other immunosuppressants such as, for example, a cyclosporin or if a rapamycin is present a FK 506 compound as described above. Cyclosporins comprise a class of cyclic, poly-N-methylated undecapeptides, generally possessing immunosuppressive, anti-inflammatory, anti-viral and/or anti-parasitic activity, each to a greater or lesser degree. The first of the cyclosporins to be identified was the fungal metabolite Cyclosporin A, or Ciclosporine, and its structure is given in The Merck Index, 11th Edition; Merck & Co., Inc.; Rahway, N.J., USA (1989) under listing 2759. Later cyclosporins to be identified are cyclosporins B, C, D and G which are also listed in the Merck Index under listing 2759. A large number of synthetic analogs are also known and representative examples are disclosed in EP 296 122, EP 484 281 and GB 2222770. These compounds are termed collectively "cyclosporins" in this specification.

The pharmaceutical composition exhibits especially advantageous properties when administered orally; for example in terms of consistency and high level of bioavailability obtained in standard bioavailability trials, e.g. 2 to 4 times higher than emulsions. These trials are performed in animals or healthy volunteers using HPLC or a specific or nonspecific monoclonal kit to determine the level of the macrolide in the blood. For example, in the test described in Example 3, 10 mg of rapamycin is administered p.o. to rats and the surprisingly high $C_{max}$ values of between 2670 and 3400 ng/ml are detected by ELISA using a specific monoclonal antibody. Also, in the test described in Example 4, an emulsion preconcentrate and a microemulsion preconcentrate composition are found to have much better pharmacokinetic properties than a standard solvent system.

Pharmacokinetic parameters, for example absorption and blood levels, also become surprisingly more predictable and problems in administration with erratic absorption may be eliminated or reduced. Additionally the pharmaceutical composition is effective with tenside materials, for example bile salts, present in the gastrointestinal tract. That is, the pharmaceutical composition is fully dispersible in aqueous systems comprising such natural tensides and is thus capable of providing microemulsion systems in situ which are stable and do not exhibit precipitation of the active ingredient or other disruption of fine particulate structure. The function of the pharmaceutical composition upon oral administration remains substantially independent of and/or unimpaired by the relative presence or absence of bile salts at any particular time or for any given individual.

The pharmaceutical composition is preferably compounded in unit dosage form, for example by filling them into orally administrable capsule shells. The capsule shells may be soft or hard gelatine capsule shells. Where the pharmaceutical composition is in unit dosage form, each unit dosage will suitably contain between 10 and 100 mg of the macrolide, more preferably between 10 and 50 mg; for example 15, 20, 25, or 50 mg of the macrolide. Such unit dosage forms are suitable for administration I to 5 times daily depending upon the particular purpose of therapy, the phase of therapy and the like.

However, if desired, the pharmaceutical composition may be in drink solution form and may include water or any other aqueous system, to provide emulsion or microemulsion systems suitable for drinking.

The utility of the pharmaceutical composition can be observed in standard clinical tests in, for example, known indications of macrolide dosages giving equivalent blood levels of macrolide; for example using dosages in the range of 2.5 mg to 1000 mg of macrolide per day for a 75 kilogram adult and in standard animal models. The increased bioavailability of the active ingredient provided by the compositions can be observed in standard animal tests and in clinical trials. If a cyclosporin or FK506 compound is included in the pharmaceutical composition, the utility may also be observed in standard clinical tests and animal models. The dosages of macrolide to be used in the clinical tests are as given above while those for the cyclosporin may be in the range of 25 mg to 1000 mg per day and those for a FK506 compound may be 2.5 mg to 1000 mg per day for a 75 kg adult.

The optimal dosage of macrolide to be administered to a particular patient must be considered carefully by the treating physician as individual response to and metabolism of the rapamycin compound may vary. It may be advisable to monitor the blood serum levels of the rapamycin compound by radioimmunoassay, monoclonal antibody assay, or other appropriate conventional means. Dosages of the macrolide will generally range from 2.5 mg to 1000 mg per day for a 75 kilogram adult, preferably 25 mg to 500 mg, with the optimal dosage being approximately 50 to 100 mg per day. Satisfactory results are obtained by administering about 75 mg per day for example in the form of two capsules, one containing 50 mg and one containing 25 mg; or three capsules each containing 25 mg. If a cyclosporin or FK506 compound is included in the pharmaceutical composition, the cyclosporin dosage may be 25 to 1000 mg per day (preferably 50 mg to 500 mg) and the FK 506 compound dosage may be 2.5 mg to 1000 mg per day (preferably 10 mg to 250 mg).

The pharmaceutical compositions are particularly useful for the following conditions:

a) The treatment and prevention of organ or tissue transplant rejection, for example for the treatment of the recipients of heart, lung, combined heart-lung, liver, kidney, pancreatic, skin or corneal transplants. The pharmaceutical compositions are also indicated for the prevention of graft-versus-host disease, such as sometimes occurs following bone marrow transplantation.

b) The treatment and prevention of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific autoimmune diseases for which the pharmaceutical compositions may be employed include, autoimmune hematological disorders (including e.g. hemolytic anemia, aplastic anemia, pure red cell anemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis.

c) The treatment and prevention of asthma.

d) The treatment of multi-drug resistance (MDR). The rapamycin compounds suppress P-glycoproteins (Pgp), which are the membrane transport molecules associated with MDR. MDR is particularly problematic in cancer patients and AIDS patients who will not respond to conventional chemotherapy because the medication is pumped out of the cells by Pgp. The pharmaceutical compositions are therefore useful for enhancing the efficacy of other chemotherapeutic agents in the treatment and control of multidrug resistant conditions such as multidrug resistant cancer or multidrug resistant AIDS.

The rapamycin compounds also exhibit anti-tumour and antifungal activity and hence the pharmaceutical compositions can be used as anti-tumour and anti-fungal agents.

In a further aspect the invention also provides a process for the production of a pharmaceutical composition as defined above, which process comprises bringing (1) a hydrophilic phase; (2) a lipophilic phase; and (3) a surfactant into intimate admixture and adding the compound of the macrolide class. When required, the composition may be compounded into unit dosage form, for example filing the composition into gelatine capsules.

Optionally further components or additives, in particular a hydrophilic phase co-component, for example ethanol, may be mixed with components (1), (2) and (3) or with or after addition of macrolide.

The composition may be combined with sufficient water or sufficient of an aqueous solvent medium such that a microemulsion or emulsion is obtained.

The contents of all the references referred to above especially the exemplified compounds are hereby incorporated by reference, and each of the exemplified compounds may be used as a macrolide in the examples listed below.

The following examples illustrate compositions in unit dosage form, suitable for use, for example in the prevention of transplant rejection or for the treatment of autoimmune disease, on administration of from 1 to 5 unit dosages/day. The examples are described with particular reference to rapamycin but equivalent compositions may be obtained employing any other macrolide.

EXAMPLE 1

Refined Glycerol-transesterified Corn Oil is Prepared as Follows:

Substantially-glycerol free glycerol-transesterified corn oil is slowly cooled to a temperature of +20° C. and kept at this temperature for one night. The corn oil is centrifuged at an acceleration of 12 000 G and at a flow rate of 103 kg/h in a continuous flow centrifuge to give a liquid phase (62 kg/h) and a sediment-containing phase (41 kg/h). The liquid phase is slowly cooled to +8° C. and kept at this temperature for one night. The liquid phase is then centrifuged at an acceleration of 12 000 G and at a flow rate of 112 kg/h to give a liquid phase (76.2 kg/h) and a sediment-containing phase (35.8 kg/h). The liquid phase is "refined glycerol-transesterified corn oil". Alternatively an improved product may be obtained by effecting the centrifugation in three steps, e.g. at +20° C., +10° C. and +5° C.

The process is characterised by a slight percentage reduction in the mono-glyceride component in the refined glycerol transesterified corn oil as compared to the starting material (e.g. 35.6% compared to 38.3%).

EXAMPLE 2

The refined glycerol-transesterified corn oil obtained as described in Example 1 is used in the preparation of the following oral unit dosage form

| COMPONENT | QUANTITY (mg/capsule) |
|---|---|
| Rapamycin | 20.0 |
| 1) Ethanol | 75.0 |
| 2) 1,2-propylene glycol | 81.0 |
| 3) refined oil | 121.5 |
| 3) Cremophor RH40 | 202.5 |
| Total | 500.0 |

The rapamycin is suspended in (1) with stirring at room temperature and (2), (3) and (4) are added to the obtained solution while stirring. The obtained mixture is filled into size 0 hard gelatine capsules and sealed using the Quali-Seal technique.

EXAMPLE 3

Pharmokinetics

Two formulations prepared as set out in Example 2 are used:

| Formulation | Component | Amount % |
|---|---|---|
| A | Tween 80 | 41.5% |
|  | Maisine | 24.9% |
|  | Propylene glycol | 16.6% |
|  | Ethanol | 15.0% |
|  | Rapamycin | 2.0% |
| B | Cremophor RH40 | 41.5% |
|  | Maisine | 24.9% |
|  | Propylene glycol | 16.6% |
|  | Ethanol | 15.0% |
|  | Rapamycin | 2.0% |

Formulation A is an emulsion preconcentrate and formulation B is a microemulsion preconcentrate. 6 male Wistar rats of mean body weight of 300 g are used per form. One day before treatment, food is withdrawn from the rats but the rats are permitted free access to water. The rats are then anesthetized by intraperitoneal injection of 2×1 ml 20% urethane and a permanent catheter is inserted into the right vena jugularis to permit blood sampling. 500 ml/animal of the formulation is administered by gastric intubation 20 hours after the surgery. A total dose of 10 mg of drug per animal is administered. Blood samples of 0.7 ml are taken from the jugular catheter of each animal 15 minutes before drug administration and then 0.17, 0.5, 1, 1.5, 2, 3, 5 and 8 hours after drug administration. The samples are kept in heparinized tubes and are analysed by means of ELISA using microtitre plates coated with rapamycin specific antibodies. The animals are killed immediately after taking the last blood sample. The results are given in the following table:

| Form | AUC (0–8 hrs) [ng · h/ml] | CV [%] | $C_{max}$ [ng/ml] | CV [%] | $t_{max}$ [hrs] | CV [%] |
|---|---|---|---|---|---|---|
| A | 11951 | 44 | 2671 | 42 | 3.8 | 29* |
| B | 13826 | 13 | 3405 | 30 | 4.0 | 35+ |

*n = 5;
+n = 2 due to difficulties with blood sampling.

The results indicate that rapamycin is well absorbed.

EXAMPLE 4

Comparison

Formulations A and B are compared to a formulation comprising 38.6% corn oil, 41.6% Labrafil M21/25C, 17.8% ethanol and 2% rapamycin (formulation C). The same procedure as used in example 3 is used except that the animals each receive a total dose of 0.5 mg of drug.

The results are given in the following table:

| Form | AUC (0–8 hrs) [ng · h/ml] | CV [%] | $C_{max}$ [ng/ml] | CV [%] | $t_{max}$ [hrs] | CV [%] |
|---|---|---|---|---|---|---|
| A | 105.8 | 28 | 31.22 | 35 | 1.6 | 51* |
| B | 96.6 | 32 | 36.13 | 60 | 0.4 | 30 |
| C | 36.2 | 31 | 7.83 | 27 | 3.0 | 78 |

*n = 4;

The results indicate that formulations A and B provide much better pharmacokinetic properties than formulation C.

EXAMPLE 5

An active compound of the FK 506 class or rapamycin class e.g. compound A is made up into a microemulsion preconcentrate having the following composition by weight 2% active compound 44% Cremophor RH40 26.4% corn-oil mono-, di-, tri-glycerides, 17.6% 1,2 propylene glycol and 10% ethanol.

What is claimed is:

1. An oral pharmaceutical composition in the form of an emulsion preconcentrate comprising rapamycin in a carrier medium which comprises 1,2-propylene glycol and a polyoxyethylene-sorbitan-fatty acid ester, wherein the emulsion preconcentrate upon contact with an aqueous medium forms an emulsion.

2. The composition of claim 1 which additionally comprises ethanol.

3. The composition of claim 1 which additionally comprises a phospholipid.

4. The composition of claim 1 which additionally comprises a mixture which is selected from the group consisting of mono-glyceride and di-glyceride; mono-glyceride and tri-glyceride; di-glyceride and tri-glyceride; mono-glyceride and tri-glyceride; and mono-glyceride, di-glyceride, and tri-glyceride.

5. The composition of claim 1 which additionally comprises an antioxidant.

6. The composition of claim 5 wherein the antioxidant is ascorbyl palmitate.

7. A composition of claim 1 in the form of a microemulsion preconcentrate.

* * * * *